United States Patent
Kurdi et al.

(10) Patent No.: US 12,233,434 B2
(45) Date of Patent: Feb. 25, 2025

(54) RAPID MERCURY-FREE PHOTOCHEMICAL MICROENCAPSULATION/NANOENCAPSULATION AT AMBIENT CONDITIONS

(71) Applicants: UNIVERSITY OF DOHA FOR SCIENCE AND TECHNOLOGY, Doha (QA); AUCKLAND UNISERVICES LIMITED, Auckland (NZ)

(72) Inventors: Jamal Kurdi, Doha (QA); Mohammed Farid, Auckland (NZ)

(73) Assignees: UNIVERSITY OF DOHA FOR SCIENCE AND TECHNOLOGY, Doha (QA); AUCKLAND UNISERVICES LIMITED, Auckland (NZ)

(*) Notice: Subject to any disclaimer, the term of this patent is extended or adjusted under 35 U.S.C. 154(b) by 127 days.

(21) Appl. No.: 18/136,106

(22) Filed: Apr. 18, 2023

(65) Prior Publication Data

US 2023/0364638 A1 Nov. 16, 2023

Related U.S. Application Data

(60) Division of application No. 17/714,874, filed on Apr. 6, 2022, now Pat. No. 11,666,940, which is a (Continued)

(51) Int. Cl.
*B05D 3/06* (2006.01)
*A61K 9/50* (2006.01)
(Continued)

(52) U.S. Cl.
CPC ............ *B05D 3/067* (2013.01); *A61K 9/5089* (2013.01); *B01J 13/16* (2013.01); *B82Y 40/00* (2013.01)

(58) Field of Classification Search
None
See application file for complete search history.

(56) References Cited

U.S. PATENT DOCUMENTS

| 4,588,639 A | 5/1986 | Ozono |
| 5,164,126 A | 11/1992 | Kalishek et al. |
| (Continued) | | |

FOREIGN PATENT DOCUMENTS

| CN | 103962075 A | 8/2014 |
| CN | 109134737 A | 1/2019 |
| (Continued) | | |

OTHER PUBLICATIONS

Supplementary European Search Report issued in corresponding European Patent Application No. 20874347.6 on Jan. 8, 2024.
(Continued)

*Primary Examiner* — Jeffrey D Washville
(74) *Attorney, Agent, or Firm* — SQUIRE PATTON BOGGS (US) LLP

(57) ABSTRACT

A method of mercury-free photochemical micro-/nano-encapsulation of an active material is a process for obtaining micro-/nano-capsules by means of curing by UV LED radiation at ambient or even cold temperatures. A stirrer photo-reactor made from glass or transparent plastics can be used but mixed flow reactor could be also employed. Appropriate mixing is sufficient to expose all droplets, which contain an active material surrounded by curable-shell materials in the emulsion to the LED radiation. Using the optimum light intensities and reactions' times is critical for encapsulating the active material with a high efficiency and producing a high quality micro-/nano-capsules, Solar monochromator device can also be used as long as it generate the same radiation with a narrow/single wavelengths as the LED device. Light emitted diode (LED) is a mercury-free UV radiation source with a long operating life time and an
(Continued)

instant ON-Off. it has a high efficiency, a very low cooling requirements and cost-efficient in photochemical encapsulation. It reduces the time of microencapsulation from 6 hours to a less than 5 minutes. It has a significant decrease in manufacturing cost, waste-water, unconverted monomers, and leftover active phase change material (PCM) compared to other methods. Conversion of more than 90% of monomers can be achieved, and encapsulation efficiency can reach 100% at optimum conditions. This is in addition to the ability of this invented technology for encapsulate volatile and heat sensitive active materials at ambient as well as low temperatures. Normal glass or transparent plastics can be used as a reactor material. Only the matched useful wavelength radiation is emitted by LED without having other wavelengths which might have a bad impact on the encapsulation process.

14 Claims, 10 Drawing Sheets

Related U.S. Application Data continuation of application No. PCT/IB2020/059540, filed on Oct. 11, 2020.

(60) Provisional application No. 62/914,149, filed on Oct. 11, 2019.

(51) Int. Cl.
  B01J 13/16 (2006.01)
  B82Y 40/00 (2011.01)

(56) References Cited

U.S. PATENT DOCUMENTS

| | | | |
|---|---|---|---|
| 2011/0119949 A1 | 5/2011 | Kites et al. | |
| 2015/0166716 A1 | 6/2015 | Madsen et al. | |
| 2017/0073610 A1 | 3/2017 | Hsu | |
| 2017/0252304 A1 | 9/2017 | Scharp et al. | |
| 2018/0223146 A1 | 8/2018 | Farid et al. | |
| 2020/0038297 A1 | 2/2020 | Demoulin et al. | |
| 2020/0385503 A1 | 12/2020 | Helgeson et al. | |

FOREIGN PATENT DOCUMENTS

| | | |
|---|---|---|
| ES | 2609285 T3 | 4/2017 |
| FR | 3066116 A1 | 11/2018 |
| WO | 2017/040699 A1 | 3/2017 |
| WO | 2017/124191 A1 | 7/2017 |

OTHER PUBLICATIONS

Database WPI, Week 201472, Thomson Scientific, London, GB; AN 2014-T00931, XP002810164, 4 pages.
Database WPI, Week 201925, Thomson Scientific, London, GB; AN 2019-05494M, XP002810165, 2 pages.
Supplemental European Search Report issued in corresponding European Patent Application No. 20874347.6-1108 on Oct. 2, 2023.
International Search Report issued in corresponding International Patent Application No. PCT/IB2020/059540 on Mar. 26, 2021.
IKA, "Accessories-Overhead Stirrers" product documentation, www.ika.com (Web archive) Jun. 17, 2019 (Jun. 17, 2019), p. 3, [online] <https://www.ika.com/en/Products-Lab_Eq/Overhead-Stirrers-Agitator-Blender-Lab-mixer-Accessories-cspacc-187/>, 16 pages.
4-Arm PEG-Acrylate, Abbexa Ltd, https://www.abbexa.com/4-arm-pag-acrylate, 4 pages.
Poshadri Achinna, "Microencapsulation Technology: A Review", https://www.researchgate.net/publication/284695566, Article Jan. 2010, J.Res.ANGRAU 38(1)86-102,2010, 18 pages.
Refat Al-Shannaq et al., "Emulsion Stability and Cross-Linking of PMMA Microcapsules Containing Phase Change Materials", Solar Energy Materials & Solar Cells 132 (2015) 311-318, www.elsevier.com/locate/solmat, http://dx.doi.org/10.1016/j.solmat.2014.08.036, 8 pages.
Professor Bohana Boh et al., "Microencapsulation by Chemical Methods: A Solution for the Past or Future", Bioencapsulation Innovations Mar. 2013, Bioencapsulation Research Group, 28 pages.
"Hymer," Borica, Jan. 23, 2023, http://www.borica.com/Hymer/hymer_app.aspx, 1 page.
Celine Dietlin et al., "Photopolymerization upon LEDs: new photoinitiating systems and strategies", Polymer Chemistry, Royal Society of Chemistry, DOI: 10.1039/c5py00258c, www.rsc.org/polymers, 18 pages.
Zhongxiang Fang et al., "Encapsulation of Polyphenols—a review", Trends in Food Science & Technology 21 (2010) 510-523, doi: 10.1016/j.tifs.2010.08.003, 14 pages.
Marta Giamberini et al., Microencapsulation, Innovative Applications, 6 pages.
Miaomiao Hu et al., "Research Advances of Microencapsulation and its Prospects in the Petroleum Industry", Materials 2017, 10, 369, MDPI, 19 pages.
A. Jamekhorshid et al.,, "A Review of Microcapsulation Methods of Phase Change Materials (PCMs) as a Thermal Energy Storage (TES) Medium", Renewable and Sustainable Energy Reviews 31 (2014) 531-542, www.elsevier.com/locate/rser, http://dx.doi.org/10.1016/jrser.2013.12.033, 12 pages.
Florent Jasinski et al., "Photopolymerizaiton in Dispersed Systems", Progress in polymer Science 84 (2018) 47-88, www.elsevier.com/locate/ppolysci, https://doi.org/10.1016/j.progpolymsci.2018.06.006, 42 pages.
Munmaya Mishra, "Handbook of Encapsulation and Controlled Release", Overview of Encapsulation and Controlled Release, CRC Press Taylor and Francis Group, http://www.taylorandfrancis.com, http://www.crcpress.com, 41 pages.
Methavee Peanparkdee et al., "Microencapsulation: A Review of applications in the food and pharmaceutical industries", Reviews in Agricultural Science, 4:56-65, 2016, DOI: 10.7831/ras.4.56, 10 pages.
Pablo Teixeira da Silva et al., "Microencapsulation: concepts, mechanisms, methods and some applications in food technology", Ciencia Rural, Santa Maria, v.44, n.7, p. 1304-1311, Jul. 2014, http://dx.doi.org/10.1590/0103-8478cr20130971, ISSN -0103-8478, 8 pages.
Maninder Singh et al., "Microencapsulation and its Various Aspects: A Review", International Journal of Advanced Research (2016), vol. 4, Issue 6, 2094-2108, http://journalijar.com, Journal DOI: 10.21474/IJAR01, ISSN 2320-5407, 16 pages.

RAPID MERCURY-FREE PHOTOCHEMICAL MICROENCAPSULATION/NANOENCAPSULATION AT AMBIENT CONDITIONS

CROSS REFERENCE TO RELATED APPLICATIONS

This application is a divisional application of U.S. patent application Ser. No. 17/714,874, filed Apr. 6, 2022, which is a filing under 35 U.S.C. § 371 of International Application No. PCT/IB2020/059540, filed Oct. 11, 2020, which claims the benefit of U.S. Provisional Application No. 62/914,149, filed Oct. 11, 2019. The entirety of each of these applications is herein incorporated by reference.

BACKGROUND OF THE INVENTION

1. Field of the Invention

The present invention relates to mercury-free photochemical micro-/nanoencapsulation, and particularly to a method for a rapid photochemical encapsulation (at micro or nano scale) of an active material at ambient conditions/low temperature, that utilizes narrow/single wavelength radiation (such as Light Emitted Diode (LED) light or solar monochromator device) at optimum light intensities and reactions' times in an appropriate stirrer or mixed flow photoreactor.

2. Description of the Related Art

Microencapsulation and nanoencapsulation are used to totally or partially isolate from the surrounding environment any active materials in a wide range of industrial applications such as energy storage using phase change materials, food, household, chemicals, additives, agrochemicals, textiles, printing, petroleum, cosmetic, medical, pharmaceutical and others [1-4]. The coated shell layer can be tailored to be a stimulus-responsive polymer or to have the ability in totally sealing or controlling the release of an active material in an ideal place at the required times [5]. The purpose of encapsulation is for obtaining the most desired characteristics and efficient usage of the active material in a given application [6].

Microencapsulation techniques can be classified into three main categories: (1) Physical mechanical methods where coating materials are formed from polymers through physical processes (such as solvent evaporation, melt solidification, . . . etc.); (2) physico-chemical methods such as sol-gel and coacervation encapsulation; and (3) chemical methods in which the coating materials are formed from monomers or oligomers through chemical reactions such as polymerization, poly-condensation, chemical curing and crosslinking. Each technique produced different microcapsules as reported elsewhere [7-9]. From these, chemical microencapsulation such as interfacial and in-situ polymerization, poly-condensation, curing and crosslinking has gained more industrial attention compared to other techniques since it produces more stable and durable microcapsules [10].

In the current art of state, physical and chemical encapsulation requires a high temperature for melting, spray drying, polymerizing, curing or crosslinking the coating materials. This will cause the following challenges:

1. Thermal microencapsulation requires a costly long reaction time (2 to 6 hours) at a high temperature (50° C. to 80° C.) [11] and hence high energy.
2. The inability for coating large number of thermo-sensitive active materials (including biomaterials) since high temperature may cause volatilization and/or destruction of these materials [5].
3. For encapsulation of PCM, the highest reported heat of fusion is 113.4 J/g when (Rubitherm® RT21). The encapsulation requires 6 hours to achieve 86.47% monomer conversion.

Chemical microencapsulation can be achieved at ambient conditions (T<40° C.) by using UV photo-initiators instead of the thermal initiators for polymerization of the coated shell layer as reported in the US patent US20180223146 [12]. In this patent, there are some major challenges for commercialization:

1. The major disadvantage of this method is using the use of UV mercury lamps, which is not energy efficient and requires cooling. In addition, useless radiation at undesirable wavelengths may have negative influence on the encapsulation process. This lamp will also be banned in the near future due to the presence of poisonous mercury.
2. The current state of art of LED technology has rapidly grown in the last few years with increasing affordable low cost and high power devices, which can be designed for desirable features such as generating a given single, or narrow wavelength range of radiation, having an adjustable light intensity up to 24 W/cm$^2$ and an instant turn on-off switch. LED has many advantages over using mercury lamps such as elimination of the radiation with undesirable wavelengths, high-energy efficiency, low waste heat (no infra-red radiations) and so low cooling requirements, low maintenance, long life, do not use poisonous mercury, and many other advantages as reported elsewhere [13]. Photopolymerization using LED has been reviewed by Dietlin et al. 2015 for various commercial photoinitiators and photocurable materials (monomers, oligomers) [14].
3. The current invention is about the use of LED in adjustable narrow/single wavelength radiation for micro-/nano-encapsulation of materials. From our literature review, the use of UV-visible LED for micro-nano-encapsulation has not yet been investigated. In our work based on "TDF1-0611-170037" project funded by Qatar foundation, we have many discoveries in the field of the micro-nano-encapsulation using LED, which are claimed in this disclosure application.

SUMMARY OF THE INVENTIONS

The method for using UV or/and Visible LED for microencapsulation or nanoencapsulation of an active core material includes the following steps: (a) preparing the discontinuous droplets phase as a mixture of active-material and curable-shell-material, which contains (1) at least one active material, (2) at least one curable material, and (3) at least one photo-initiator without or with redox photoinitiators or other types of photoinitiators at a concentration as provided by supplier. The weight of the droplets discontinuous phase is typically around 18% of the weight of the continuous phase; however, a lower or higher percentage can also be used depend on the required application. Commercial phtocurable materials or any other curable materials disclosed in literature can be selected based on the desired characteristics of the required micro-/nano-capsules in a given application. (b) preparing the continuous phase from a liquid which is immiscible with the discontinuous droplets phase. The continuous liquid phase contains at least one stabilizing/emulsifying agent at a concentration as provided by supplier. (c) preparing the micro-nano emulsion by emulsifying the mentioned discontinuous droplets phase in the mentioned continuous phase for a desirable droplet size by controlling the degree of emulsification and by introducing sonication if a nanoscale droplet size is required. (d) exposing the prepared emulsion by UV-Visible LED in a stirred batch or continuous mixed flow photoreactor; and (e) curing the shell-material layer of each droplet using at least one UV or/and Visible LED lamp at optimum wavelengths, light intensities and reactions times for complete conversion of all curable-material, and full encapsulation of the active material. The selection of the weight ratio of the active material to the curable shell-material is critical (typically in the range between 1:1 and 2:1 or others) to obtain the maximum content of the active material in the micro-/nano-capsules; and at the same time, maximizing the conversion of the curable shell material.

A stirrer LED photoreactor for micro-/nano-encapsulation of an active material may be consists of rounded or square tubes made from a glass or plastic, which is transparent to the radiation within the desired wavelengths. The encapsulation can be completed in the stirrer photoreactor in a batch or continuous flow process. Based on the optimum processing conditions, radiation intensity can be changed, and different irradiation time periods can be used. More than one LED lamp each having a different or similar light wavelength and different light intensity, or even more than one photoreactor can be used. Such a reactor is easy to scale-up for a large industrial production by simply increasing the length of the tubes, increasing the number of lamps and/or increasing the number of tubes. Although, we did not use nitrogen purging to exclude the presence of oxygen, it may be necessary to include that in some application. Appropriate pump for a continuous flow encapsulation, light sensors, and in situ reaction analyzers, could be included based on the required needs of a given application. FIG. 1. Show an example for the LED photo-reactor setting. Two identical LEP lamps are used. The stirrer design is very critical to have sufficient mixing without causing a damage to the microcapsules particularly during the initial time of curing the shell layers of the microcapsules. Other arrangements such as thin-film flow photo-reactor developed in our previous inventions [12] can also be used and optimized.

DETAILED DESCRIPTION OF THE PREFERRED EMBODIMENTS

The method for mercury-free photochemical micro-/nano-encapsulation of an active material is a process for obtaining micro-/nano-capsules by means of curing by LED radiation at ambient or even cold temperatures. A stirrer photo-reactor made from glass or UV or/and visible transparent plastics can be used. Appropriate mixing is sufficient to expose all droplets, which contain an active material surrounded by curable-shell materials in the emulsion to the LED radiation. Using the optimum light intensities and reactions' times is critical for encapsulating the active material with a high efficiency and producing a high quality micro-/nano-capsules. Solar monochromator device can also be used as long as it generates the same radiation as the LED device. Compared to using medium pressure mercury lamp or thermal encapsulation, encapsulation using UV-LED is more energy efficient, more environment friendly, radiation with undesirable wavelengths can be excluded and also simple to arrange (no purging with nitrogen, no purification for the used technical materials, not using quartz reactor and so on).

The method for using LED for microencapsulation or nanoencapsulation of an active core material includes the following steps: (a) preparing the discontinuous droplets phase as a mixture of active-material and curable-shell-material, which contains (1) at least one active material, (2) at least one curable material, and (3) at least one photoinitiator without or with redox photoinitiators or other types of photoinitiators. (b) preparing the continuous phase from a liquid which is immiscible with the discontinuous droplets phase. The continuous liquid phase contains at least one stabilizing/emulsifying agent. (c) preparing the micro-nano emulsion by emulsifying the mentioned discontinuous droplets phase in the mentioned continuous phase for a desirable droplet size by a high shear emulsifier. (d) introducing the prepared emulsion into a stirrer photoreactor, while stirring the emulsion at an appropriate speed; and (e) curing the shell-material layer of each droplet using at least one LED lamp at optimum light intensities and reactions' times for complete conversion of all curable-material, and full encapsulation of the active material.

The process of microencapsulation of an active material is based on LED as a narrow or single wavelength radiation. We have discovered that a low or high intensity of radiation leads to reduce significantly the efficiency of the encapsulation process and the quality of the produced capsules. In addition, we have discovered that each stage of the encapsulation process may require a different radiation intensity for an optimum period. In other word, the encapsulation process can be implemented under an optimum constant or changeable intensity of radiation at an optimum wavelength for an optimum period. Using a longer time of ray irradiation than the optimum for each stage process or the entire process may lead to a significant bad influence on the produced capsules. The optimum conditions and processing time depend on the formula of the curable materials, photoinitiators, boost/enhance processing additives, stabilizer/emulsifying agents and emulsion preparation method. In most cases, the total period of encapsulation process is less than 5 minutes. The encapsulation process is implemented at ambient temperature, but also can be done at other temperatures particularly at a colder temperature than the room temperature, if there is a need for this.

The active material can be a known organic phase change material or any active material used in food, household, chemicals, additives, agrochemicals, textiles, printing, paint, petroleum, cosmetic, detergent, medical, pharmaceutical and others.

The droplet stabilizer typically is any polymer with an interface (hydrophobic/hydrophilic) activity such as polyvinylalcohol, polyvinylpyroolidone, and commercial G-Polymer(BVOH) with adding any type of commercial surfactants at their optimum concentrations. Also, modified stabilizers such as the commercial Gohsenx (modified PVOH) L-3266 can be used without the need for using surfactants.

The process of encapsulation of an active material can further include adding at least one of the di-functional, tri-functional, polyfunctional or oligomers to the monomer, wherein the curable component is selected from the group consisting of an organic material with polymerizable functional groups such as acrylates, urethane, urea-formaldehyde, mixtures thereof. The monomer is an unsaturated polymerizable organic compound, which is typically used in any polymeric coating.

The process of encapsulation of an active material can further be improved by adding additive that use for eliminating oxygen inhibition, accelerate encapsulation process, enhance obtaining the desirable characteristics of the required quality of the capsules. These additives is selected from the group consisting oxygen (ethers) or nitrogen (amines, amino-monomers), sulfur (thiols), redox initiators or other commercial available additives.

The produced capsules requires filtration or centrifugal separation, washing, and drying at 55° C. for at least 12 hours.

The process of separation of the nanocapsules form the product of the photoreactor is difficult to achieve by vacuum filtration. Centrifugal separation is suitable for separation of the nanocapsules as well as for the microcapsules but any other method of separation could be applied.

Typically, in an exemplary embodiment, the stirrer photoreactor designed in this work for LED micro-/nano-encapsulation of an active material includes a glass or plastic tubes (transparent to the radiation within the desired wavelengths), appropriate adjustable stirrer, and LED lamps for curing the shell layer of the capsules. Described below is an exemplary method to produce the capsules using stirrer LED photo-reactor. These examples should not limit the scope of the inventions mentioned. Other photo-reactor designs where mixing cause an optimal expose of the entire emulsion for irradiation could be employed.

EXAMPLE 1

A Stirrer Photoreactor for Microencapsulation of Commercial Rubitherm® RT21

The RT21 microcapsules were prepared in a stirrer photoreactor. As shown in FIG. 1, the LED stirrer photoreactor consists of a pyrex rounded glass tube with 3.5 cm diameter and 13 cm height. Two identical LED lamps (BETTSENS) at a wavelength of 365 nm and adjustable radiation intensity between 0 and maximum 12 W/cm$^2$ are contact to the outside of the tube. The light emitted area of each lamp is (11×1.5 cm). The second lamp is turned 90 degree in reference to the first lamp as shown in FIG. 1. A helix stirrer that fit inside the tube is used. In one of the typical experiment, the curable materials consists of a hard-monomer such as MethylMethAcrylate (MMA) or soft-monomer such as Butyl acrylate (BA) or their mixture at a concentration of 70% by weight and 30% by weight of di-tri and/or polyfunctional monomers or oligomers. For a thick layer of curable materials, acylphosphine oxides are very effective photoinitiators. In this example, commercial bis-acylphosphine oxide (Irgacure 819, BAPO) was used at a concentration of 3% by weight of curable materials. The weight ratio of Rubitherm® RT21 to the curable materials is 1. Deionized water was used as a continuous phase in the emulsion with a stabilizer such as the commercial Gohsenx (modified PVOH) L-3266 at a concentration of 1% by weight of the total aqueous phase. This can produce a surfactant-free emulsion. The organic phase and aqueous phase were emulsified using a high shear emulsifier at a speed of 4500 rpm for 30 minutes. The Pyrex glass tube was filled with the emulsion, and the irradiation by the two LED lamps was applied while mixing the emulsion. The produced microcapsules were separated from the suspension by filtration, washed and dried in an atmospheric oven at 55° C. for at least 12 hours. Additional drying for a long time also was applied. Microcapsules drying at different time were tested.

Experiments in example 1 were conducted at technical conditions without any improvement in order to be compared with the traditional thermal encapsulation. For instance, all curable materials were not purified (i.e. the hydroquinone inhibitor was not removed from the monomers), purging with nitrogen was not used, Pyrex glass tube was used without the need for an expensive quartz tube, enhancement additives were not added, and the weight ratio of the active material (RT21 in this example) to the curable shell materials was not optimized. The results from example 1 was excellent compare to the thermal encapsulation as shown in FIG. 2. Room temperature was used during encapsulation instead of 80° C. Total encapsulation time was reduced from 6 hours to 4 minutes.

All PCM (100%) is encapsulated while in the thermal method, up to 98.5% of PCM is encapsulated. The monomer conversion and the total yield of the product is 79.82% (w/w) and 89.57% (w/w) respectively. The thermal method has a higher monomer conversion and total yield by less than 7%. However, the heat of fusion of the dried microcapsules is 123.96 J/g (in example 1, FIG. 2), which significantly higher than those commercially available. It is clear from the SEM image in FIG. 2 that most of the microcapsules are deflated as indicated by the axisymmetric dimple forms on one side of the spherical shells. Buckling of the spherical shell of the microcapsules might be attributed to the reduction of the volume inside the capsules during drying process or because of the collusion among capsules as a result of mixing while encapsulation. However, the increase in the heat of fusion of the PCM-microcapsules upon drying at 55° C. for 20 days indicates that the PCM is well contained. Also, none of the capsules are broken, and there is a possibility that some non-polymerized monomers such as MMA is entrapped inside the capsules with the PCM. Upon drying for long time, MMA is a volatile component would evaporate to outside of the capsules causing a decrease in the volume of the core materials. Most probably, PCM to curable materials ratio should be increased in order to optimize the use of the extra non-polymerized monomers. The thickness of the shell curable materials depends on both the ratio of PCM to the curable materials and the size of the microcapsules. In fact, the size of the microcapsules can be controlled by adjusting the speed of the emulsifier and the use of the sonication. It can be concluded that for each desirable capsule' size, there is an optimum ratio of the active material to the curable shell material. This optimum ratio is different for different capsules' sizes.

EXAMPLE 2

Microencapsulation of Puretemp®20 (PT20) Using Thin-Film Flow Photo-Reactor

The reactor, as shown in FIG. 3, consists of an LED panel, which emits UV light of the wavelength 365 nm. It also includes a peristaltic pump that pumps the feed to a UV reaction box through a flow distributor. The UV reaction box has a flow distributor to ensure the laminar flow of the feed on the bottom plate made of quartz. The light from the UV-LED panel is incident on this bottom plate. The upper plate of the UV reactor box is a reflecting surface to ensure maximum exposure of UV light to the feed. The feed is purged with nitrogen gas throughout the experiment, and the feed is under continuous recirculation. The flow of the feed is maintained to about 300 ml/min. The setup also includes an exhaust fan to ensure there is no overheating. All the inner surfaces of the reactor were lined with aluminum sheets to contain the scattered light.

Methods

1) Emulsification

The emulsification process of aqueous and organic phases was carried out using the proportions stated in Table 1. A Silverston LSM, high shear mixer with a fine screen was used for the emulsification process. The rate of mixing was set to 4000 rpm for all samples unless otherwise mentioned.

TABLE 1

Chemical recipe of ingredients for emulsion preparation.

| | Compound | Weight (g) |
|---|---|---|
| Aqueous Phase | Deionized water | 400 |
| | Polyvinyl alcohol (PVA) | 4 |
| | Sodium dodecyl sulphate (SDS) | 0.2 |
| | Methyl Methacrylate (MMA) | 24.71 |
| | Ethylene glycol dimethacryalte (EGDM) | 8.43 |
| Organic Phase | Pentaerythritol triacrylate (PETA) | 2.05 |
| | Puretemp ®PT20 (PCM) | 35.73 |
| | IRGACURE 819 (photoinitiator) | 1.03 |

2) Photo-Induced Polymerization

The encapsulation was carried out in the UV-LED reactor. The flow rate of 300 ml/min was chosen to ensure sufficient exposure time and flow as a thin laminar film. High power (450 W) and low power (150 W) of UV light incidence were tested as parameters for different treatment times in this experiment. The treatment times of 10 min, 20 min and 30 min were selected for each power. Additional treatments of 1 min, 2 min and 5 min were also conducted for the UV power of 450 W. Each sample was then centrifuged at 10000 rpm for 10 min. The cake formed was separated to procure the microcapsules. The microcapsules were washed with n-hexane to remove the unreacted monomer and unencapsulated PCM. Finally, the washed microcapsules were dried in a hot air oven at 50° C. overnight before further analysis. Results show high quality microcapsules. Lower UV intensity showed a reasonable microencapsulation. However, the use of treatment intensity of 450 W (one lamp) did not only give high-quality PCM microcapsules with about ≈70% PCM content, but it was possible to reduce treatment time to as low as 1.0 min.

FIG. 4 show the DSC diagram of pure PT 20 PCM used in the encapsulation showing 165 J/g latent heat of melting. The corresponding latent heat of melting for different doses of UV (different treatment times) are shown in FIG. 5, showing latent heat of melting as high as 120 J/g, even for very short treatment time of 1 min only. The TGA of the microcapsules shown in FIG. 6 indicate the quality of the capsules for the 1 min is as good as those produced with longer treatment time. FIG. 7 is the strong evidence of the quality of the microcapsules since they showed stable mass when left in oven at 50 C for extended period. The initial loss is not PCM loss but rather the external solvent and water at the surface of the capsules.

EXAMPLE 3

Effect of Radiation Intensity on Encapsulation Efficiency for 2 Minutes Reaction Time at a Wavelength of 365 nm The same experimental procedures in example 1 was used in example 1. The encapsulation efficiency (total yield) were determined at different constant radiation intensities as shown in FIG. 8.

It is clear that there is an optimum radiation intensity where the encapsulation efficiency can be optimized. This indicates that not only matching the wavelength that the photo initiator will absorb is required but also, we should match the intensity of radiation, which can be absorbed by the required photo reaction. The peak represents the optimum radiation intensity. Below or above this optimum intensity, the encapsulation efficiency is significantly decreased.

EXAMPLE 4

Effect of Irradiation Time on Encapsulation Efficiency at a Radiation Intensity of 1.2 W/cm$^2$ (10% of the Maximum) and a Wavelength of 365 nm The same experimental procedures in example 1 was used in example 4. The encapsulation efficiency (total yield %) were determined at different irradiation time at a wavelength of 365 nm and a radiation intensity of 1.2 W/cm$^2$ as shown in FIG. 9.

Increasing the time more than the required time for the encapsulation reaction may lead to ruin the capsules. This is because the radiation will not be absorbed; and its action might be in ruin or reverse the encapsulation reaction.

EXAMPLE 5

Effect of Irradiation Time on Encapsulation Efficiency at a High Radiation Intensity of 12 W/cm$^2$ (Maximum Light Intensity of the LED Lamps) and a Wavelength of 365 nm The same experimental procedures in example 1 was used in example 5. The encapsulation efficiency (total yield %) were determined at different irradiation time at a wavelength of 365 nm and a radiation intensity of 12 W/cm$^2$ (maximum light intensity of the LED lamps) as shown in FIG. 10.

It is clear that the encapsulation efficiency increases in the first 40 seconds, and then the high light intensity starts to have more ruin action on the encapsulation process with time. The encapsulation efficiency (total yield %) at the maximum light intensity of the LED lamps does not exceed 25%. Waxy appearance of the capsules indicates that the PCM does not encapsulated. This example is only to show the bad influence of the high light intensities particularly on the early stage of encapsulation.

EXAMPLE 6

Effect of Decreasing or Increasing the Light Intensity on the Encapsulation Efficiency at a Wavelength of 365 nm, and Total 6 Minutes Irradiation Time The same experimental procedures in example 1 was used in example 6. The encapsulation efficiency (total yield %) were determined at different irradiation time and different intensities at a wavelength of 365 nm as shown in Table 2.

TABLE 2

Encapsulation efficiency at decreasing and increasing light intensities for total irradiation of 6 minutes, which is divided into two stages.

| Light Intensity Time | Encapsulation |
|---|---|
| 100% & 10% 3 minutes each | 34.7 |
| 10% & 100% 3 minutes each | 87.5 |
| 100% & 10% 4 minutes & 2 minutes | 25.5 |
| 10% & 100% 4 minutes & 2 minutes | 78.2 |

The encapsulation efficiency is low when it is started with a high light intensity (100%). Further reduction occurs when the 100% intensity is used for a longer time (4 minutes instead of 3 minutes). Switching to a lower light intensity (10%) does not improve the efficiency. Starting with low light intensity was useful in increasing the encapsulation efficiency. However, switching to 100% to 10% intensity after 3 minutes will lead to a higher efficiency than switching after 4 minutes. This means that each stage at a certain light intensity has an optimum period of time. Using a long time in any of the stages might have a negative influence on the encapsulation process. This is similar to thermal microencapsulation, since good capsule can be produced on when polymerization temperature was kept low initially to give sufficient time for the proper shell to form. Hence in the UV-LED microencapsulation, it is necessary to start with a low radiation intensity and then increase it to a high level.

EXAMPLE 7

Effect of Irradiation Time on Encapsulation Efficiency at a Radiation Intensity of 0.6 W/cm² (5% of the Maximum) and a Wavelength of 365 nm The same experimental procedures in example 1 was used in example 7. The encapsulation efficiency (total yield %) were determined at different irradiation time at a wavelength of 365 nm and a radiation intensity of 0.6 W/cm² as shown in FIG. 11.

As shown in FIG. 11, increasing the irradiation time to 5 minutes at radiation intensity of 0.6 W/cm², it is possible to obtain encapsulation efficiency (total yield) of 95.9% and 100% PCM efficiency. The heat of fusion is 112.51 J/g when Rubitherm® RT21 as a PCM material is used. It needs 5 minutes reaction time to achieve 91.8% monomer conversion. These results are outstanding compare to all results found in literature and mentioned in the section 2. Description of the related art.

LIST OF TABLES

Figure 1:
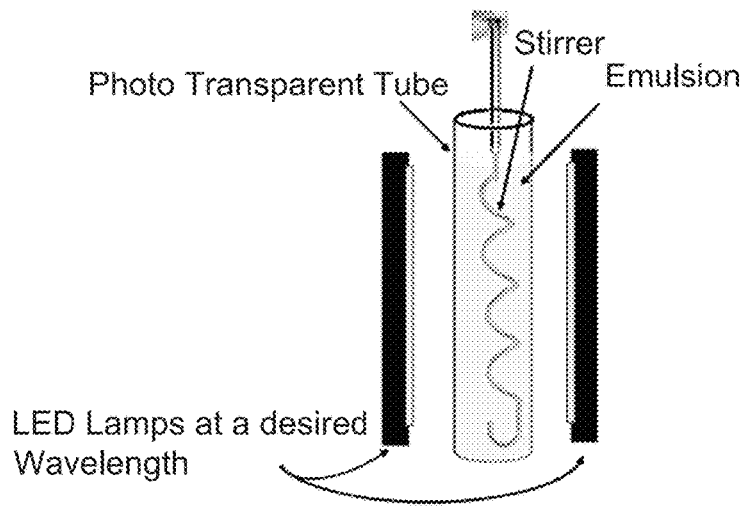
FIG. 1: photochemical stirrer reactor for micro- and nano-encapsulation.
Figure 2:
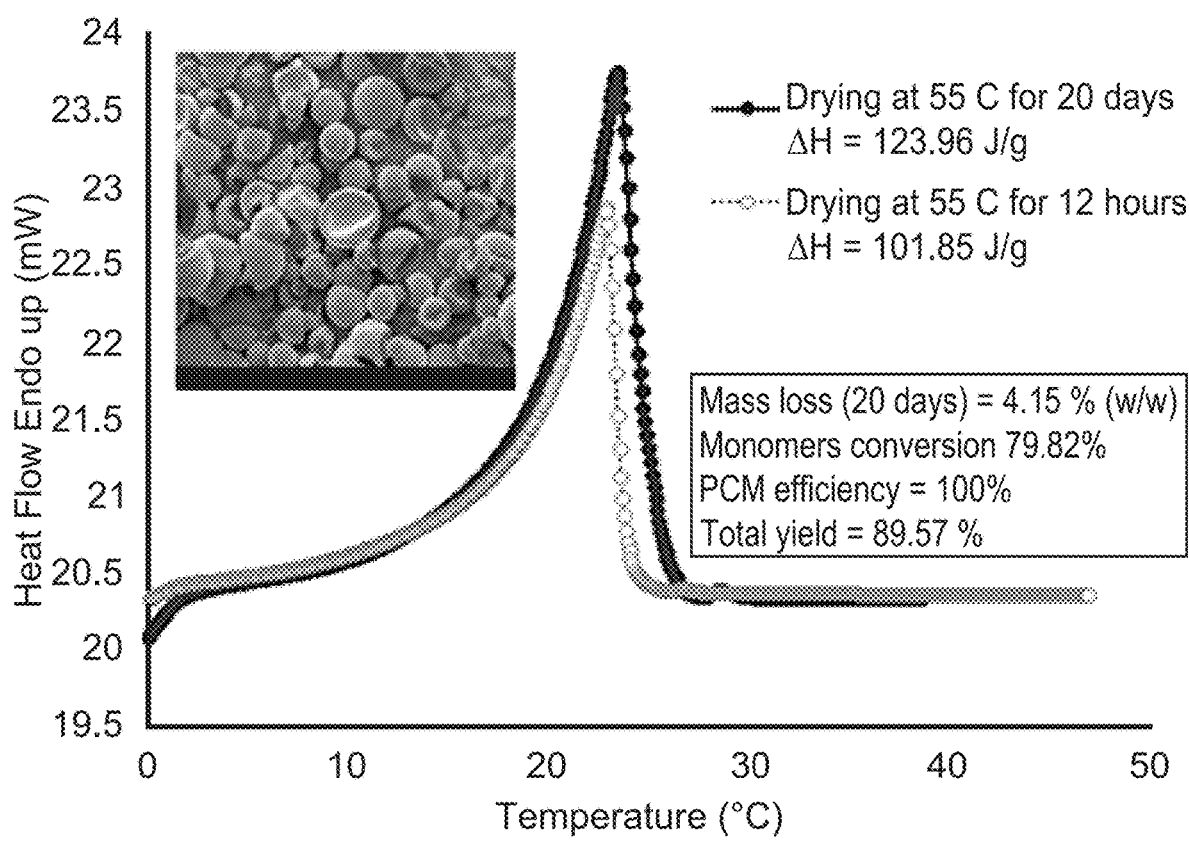
FIG. 2: Heat of Fusion of PCM Microcapsules drying at 55° C. for 12 hours and then, after drying at 55° C. for 20 days. Irradiation at 1.2 W/cm² for 4 minutes.
Figure 3:
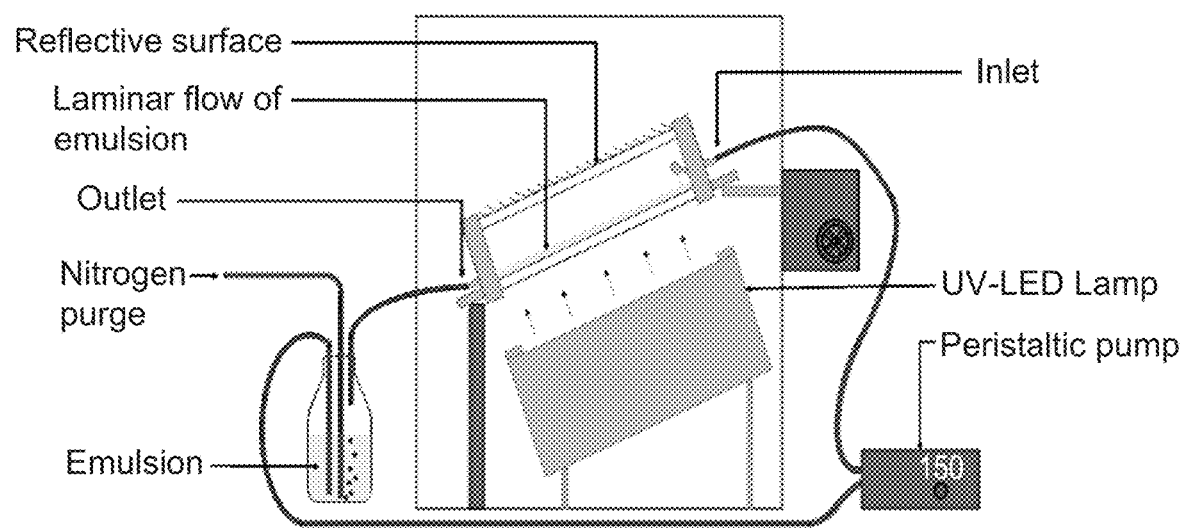
FIG. 3: photochemical thin-film flow reactor for micro- and nano-encapsulation
Figure 4:
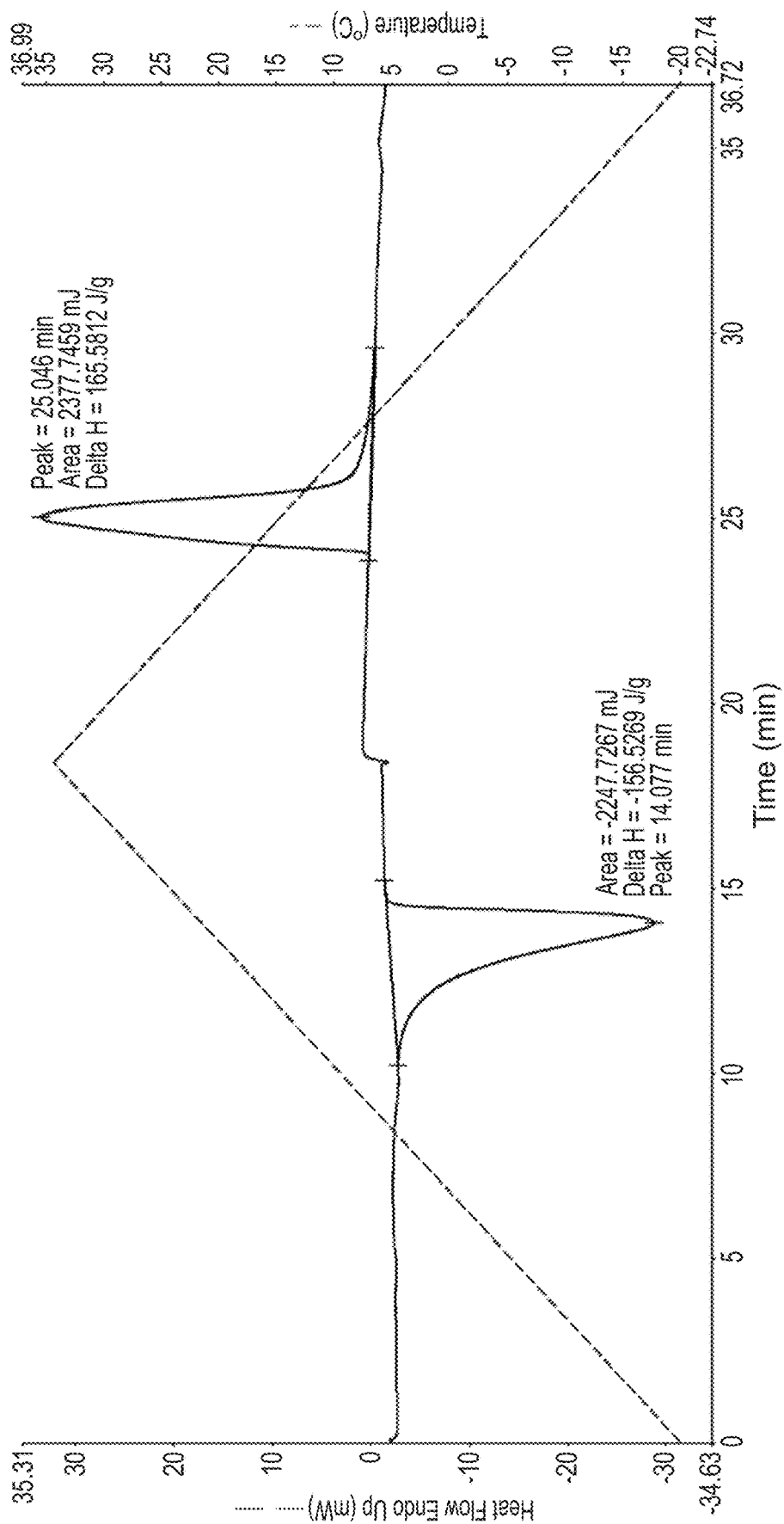
FIG. 4: DSC thermogram of pure PT 20.
Figure 5A:
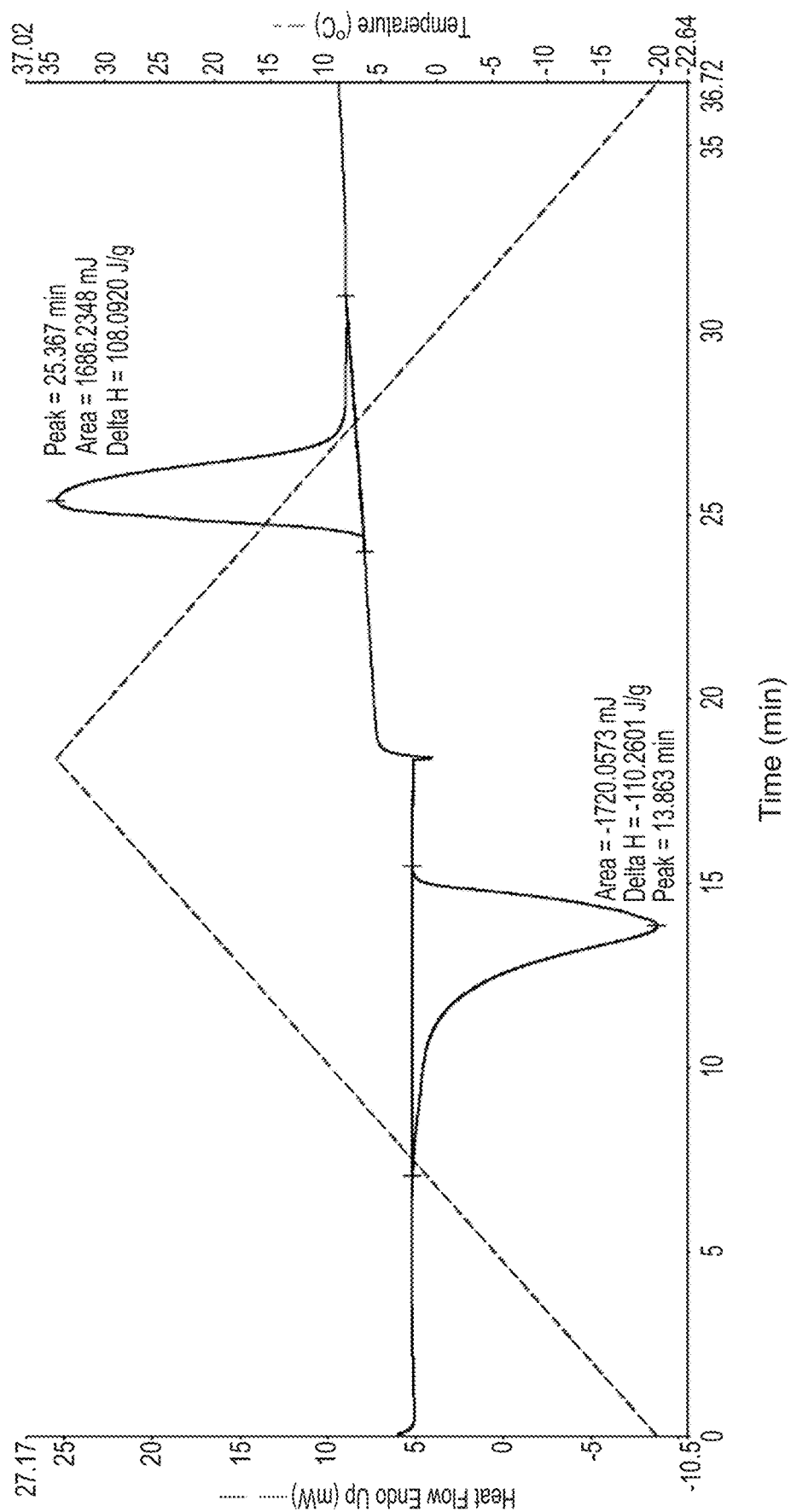
FIG. 5A: DSC measurements of microcapsules treated at 450 W UV intensity for 1 min.
Figure 5B:
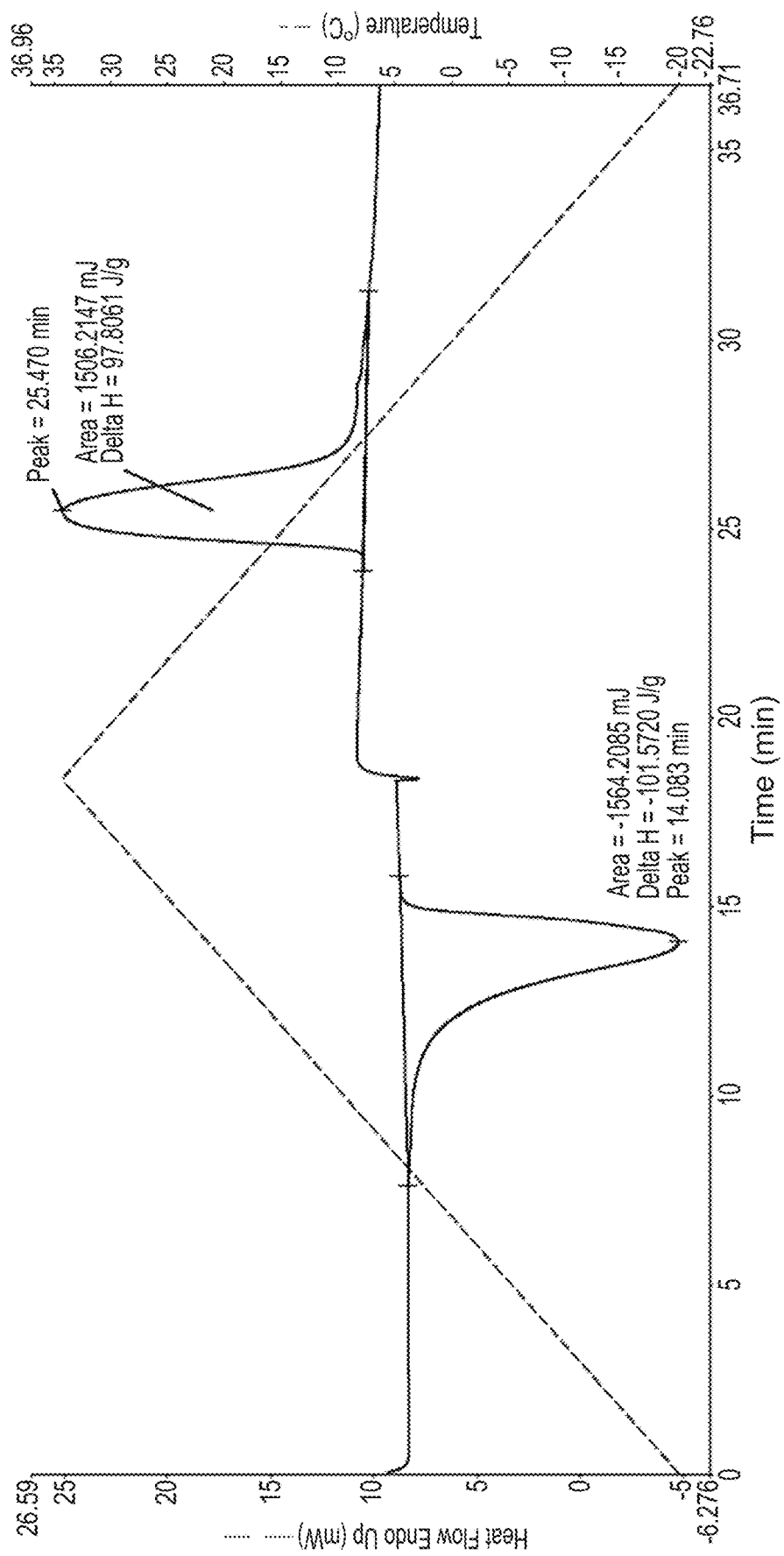
FIG. 5B: DSC measurements of microcapsules treated at 450 W UV intensity for 2 min.
Figure 5C:
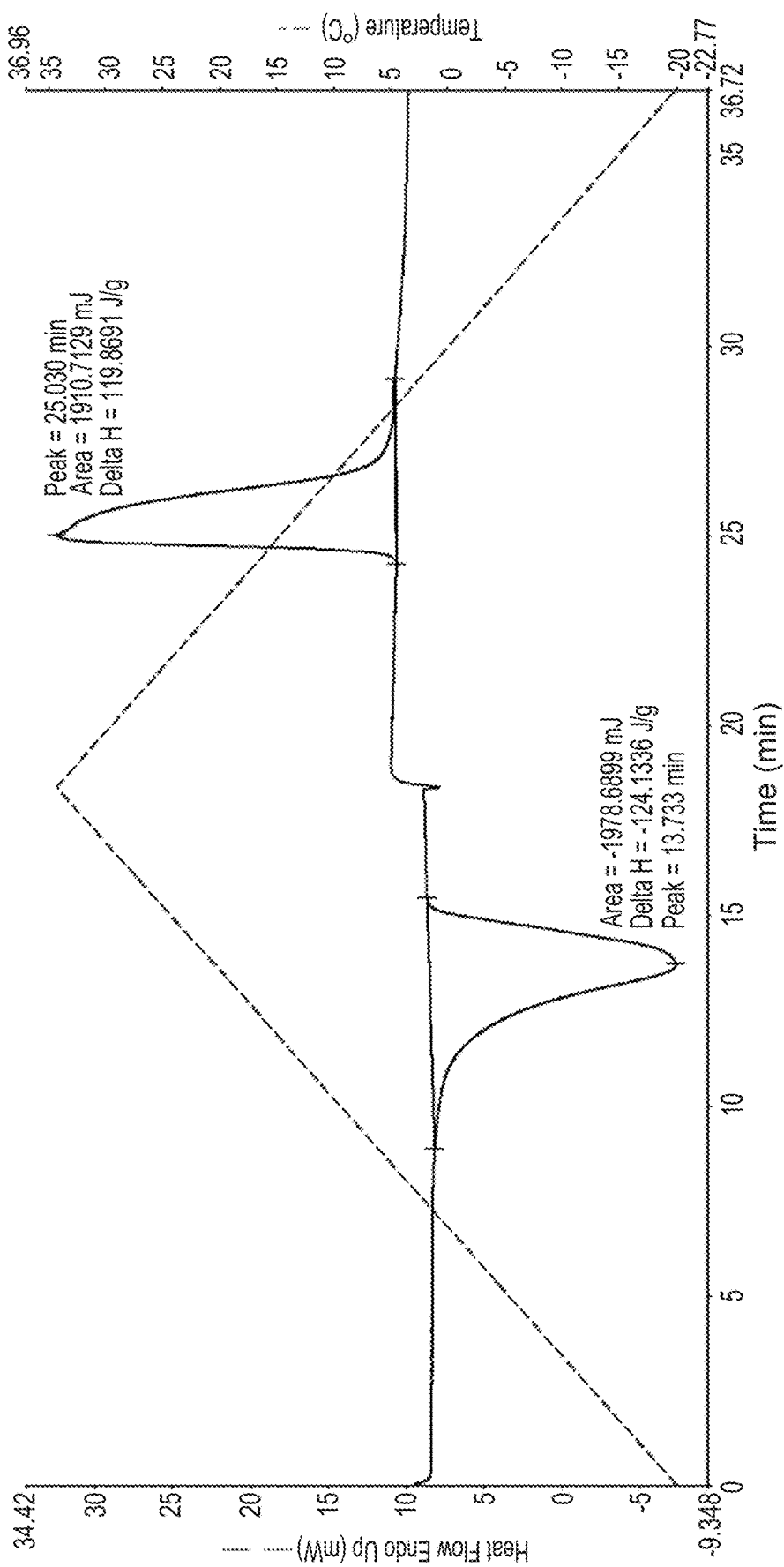
FIG. 5C: DSC measurements of microcapsules treated at 450 W UV intensity for 5 min.
Figure 5D:
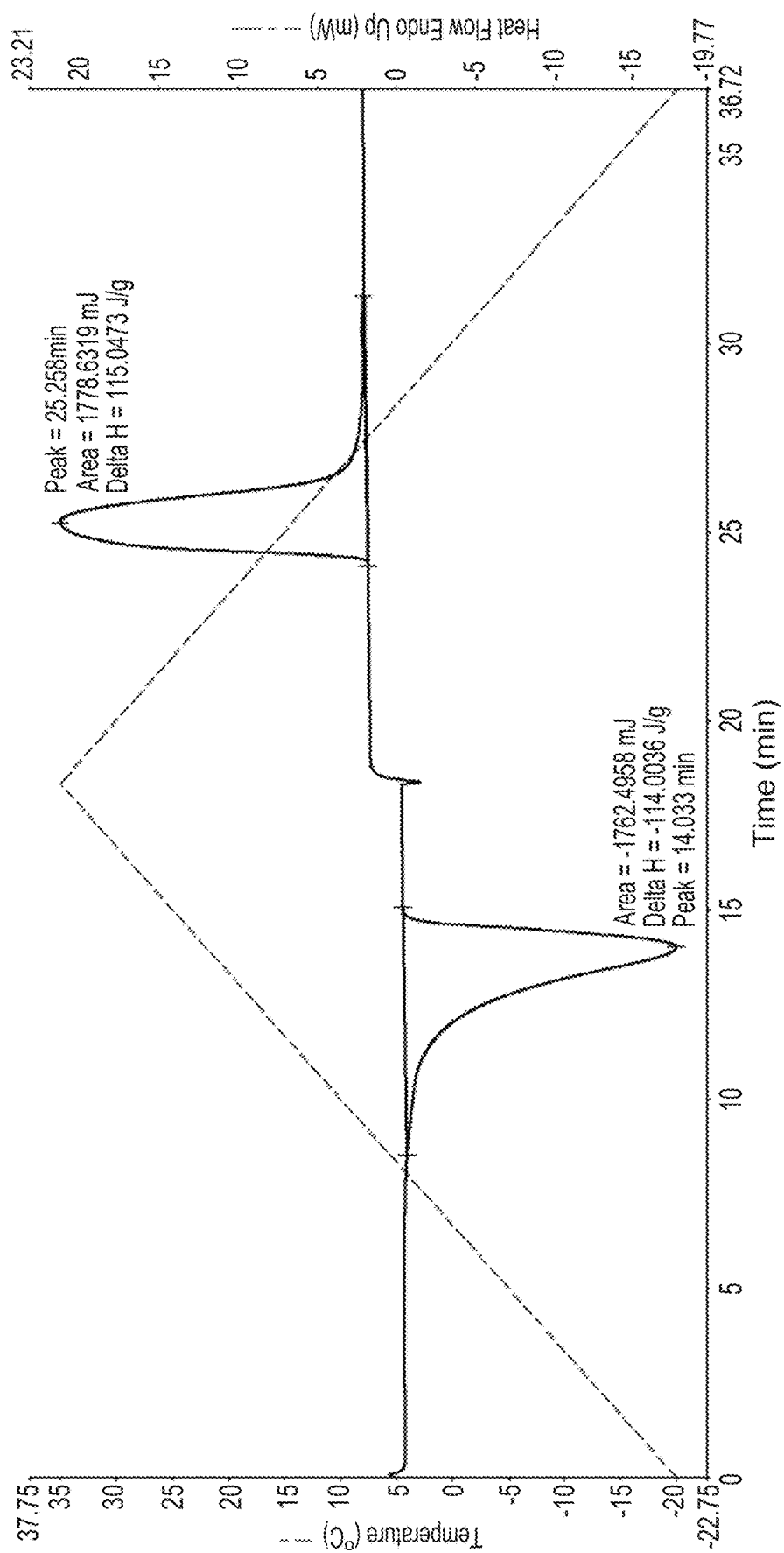
FIG. 5D: DSC measurements of microcapsules treated at 450 W UV intensity for 10 min.
Figure 6:
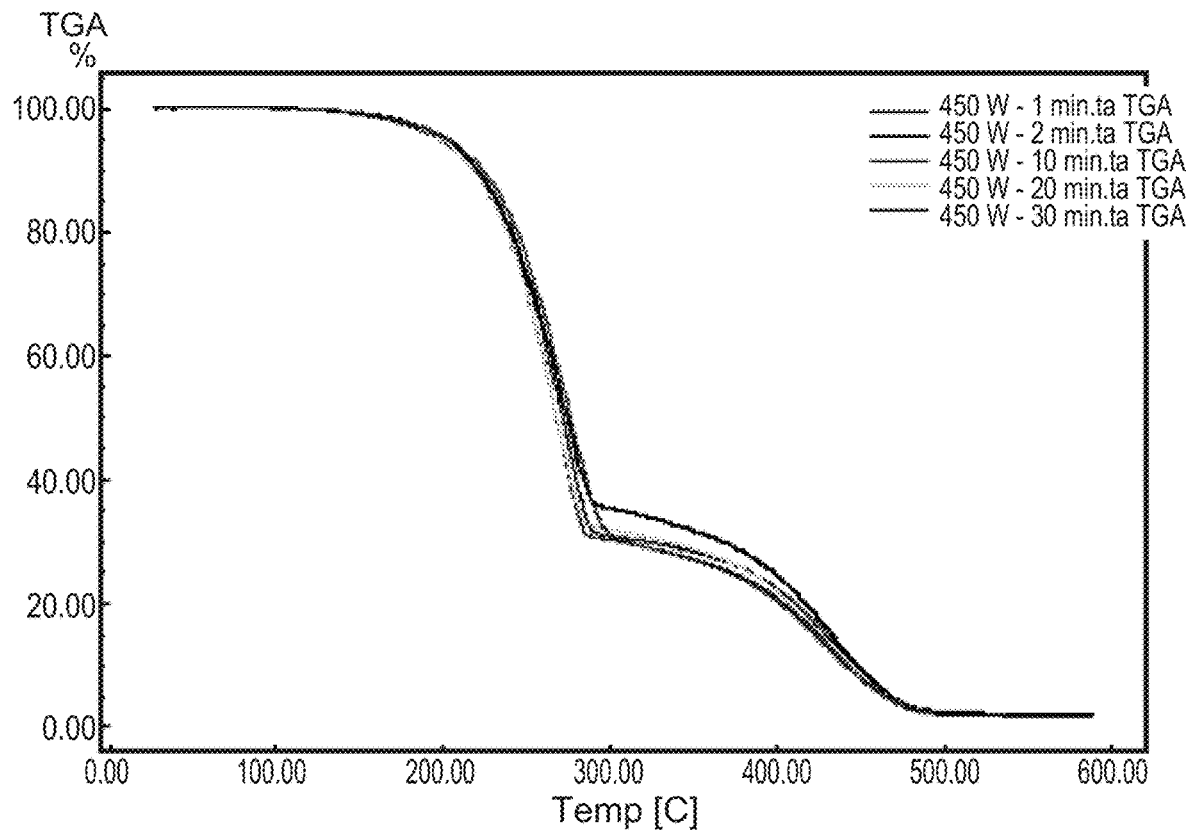
FIG. 6: Thermogravimetric analysis of samples treated at UV intensity of 450 W.
Figure 7:
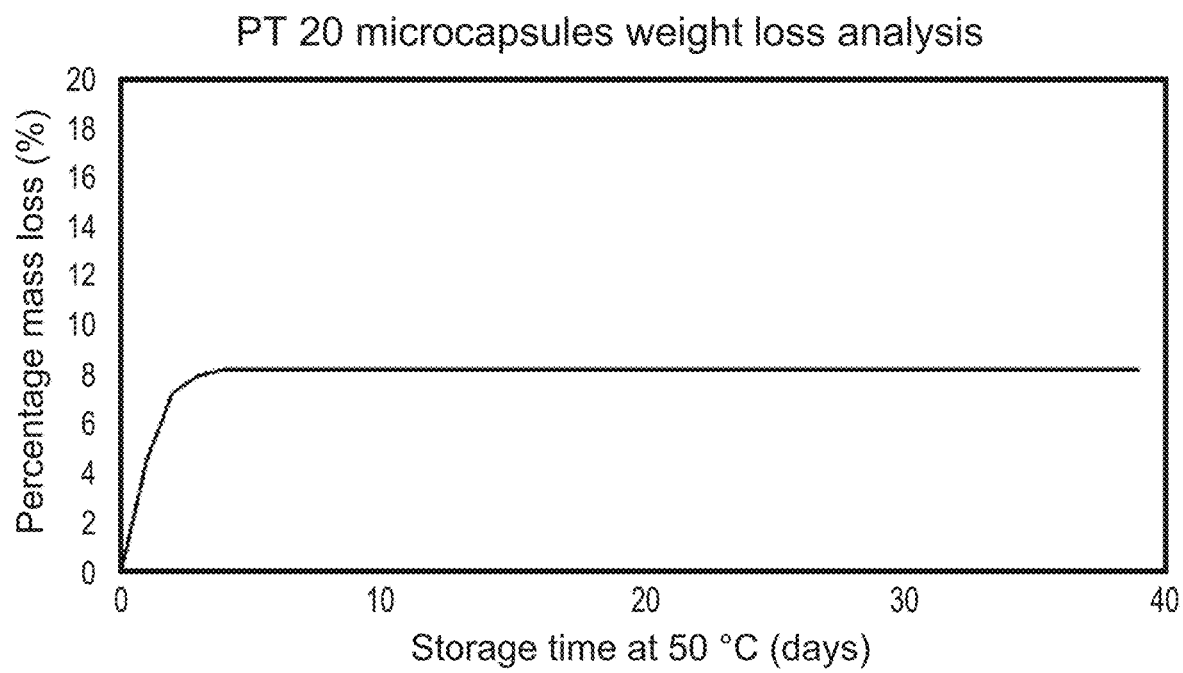
FIG. 7: Weight analysis of PT 20 microcapsules stored at 50° C. over a span of 40 days.
Figure 8:
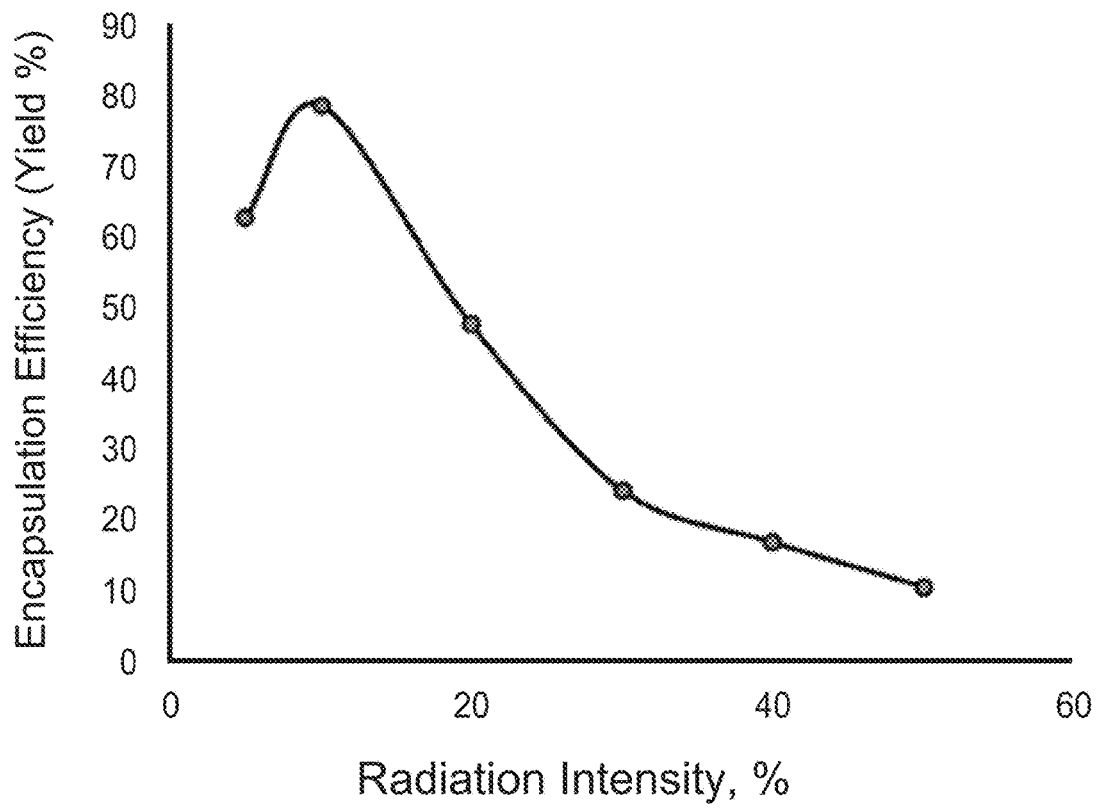
FIG. 8: Influence of Radiation intensity on encapsulation efficiency for 2 minutes reaction time at wavelength of 365 nm.
Figure 9:
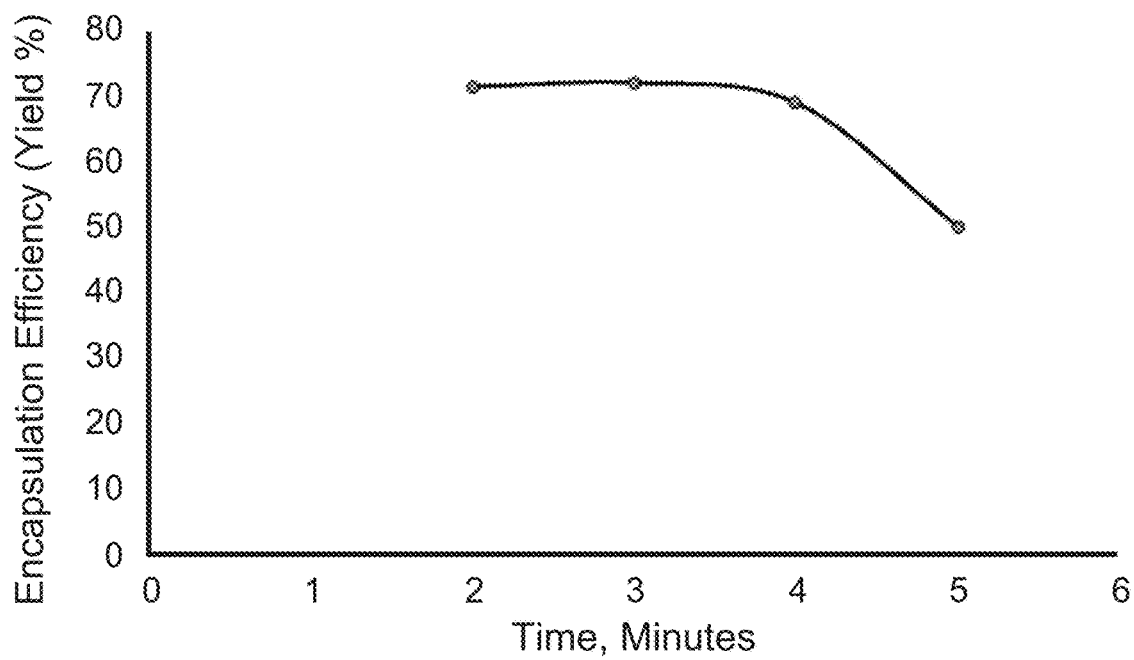
FIG. 9: Influence of irradiation time on encapsulation efficiency without using the mixer in the photoreactor at a wavelength of 365 nm and a radiation intensity of 1.2 W/cm².
Figure 10:
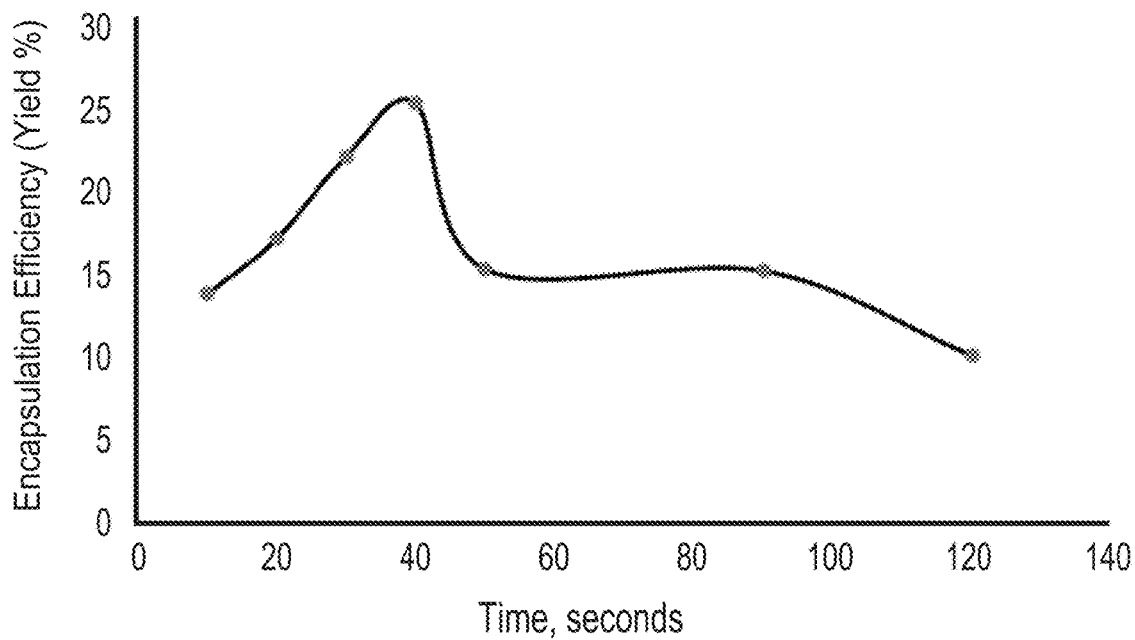
FIG. 10: Influence of irradiation time on encapsulation efficiency at a wavelength of 365 nm and a radiation intensity of 12 W/cm² (maximum light intensity of the LED lamps).
Figure 11:
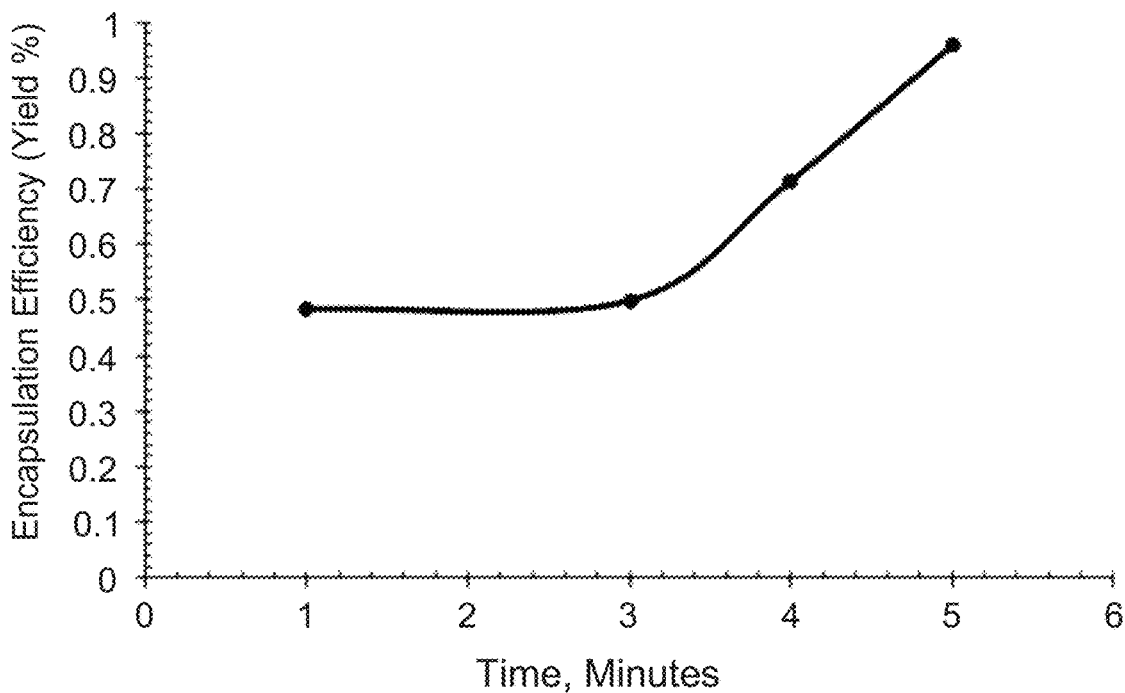
FIG. 11: Influence of irradiation time on encapsulation efficiency at a wavelength of 365 nm and a radiation intensity of 0.6 W/cm².

Table 2: Chemical recipe of ingredients for emulsion preparation

Table 2. Encapsulation efficiency at decreasing and increasing light intensities for total irradiation of 6 minutes, which is divided into two stages.

REFERENCES

[1] Maninder Singh, J. S. Dua, Muse Menra, Mansi Soni and D. N. Prasad; Microencapsulation And Its Various Aspects: A Review, International Journal of Advanced Research (2016), Volume 4, Issue 6, 2094-2108.

[2] Mishra, Munmaya (Editor), Handbook of Encapsulation and Controlled Release, book Published by CRC Pr I Llc (2015), ISBN 10: 1482232324 ISBN 13: 9781482232325

[3] Giamberini (2015) Microencapsulation: Innovative Applications; Ed. by Giamberini, Marta/Fernandez Prieto, Susana/Tylkowski, Bartosz; November 2015, ISBN 978-3-11-033199-8.

[4] Miaomiao Hu, Jintang Guo, Yongjin Yu, Lei Cao and Yang Xu; Research Advances of Microencapsulation and Its Prospects in the Petroleum Industry; Materials 2017, 10(4), 369; doi:10.3390/ma10040369

[5] Silva, Pablo Teixeira da, Fries, Leadir Lucy Martins, Menezes, Cristiano Ragagnin de, Holkem, Augusto Tasch, Schwan, Carla Luisa, Wigmann, Évelin Francine, Bastos, Juliana de Oliveira, & Silva, Cristiane de Bona da. (2014). Microencapsulation: concepts, mechanisms, methods and some applications in food technology. Ciência Rural, 44(7), 1304-1311. https://dx.doi.org/10.1590/0103-8478cr20130971

[6] Poshadri A. and Aparna Kuna. Microencapsulation Technology: a review, J.Res. ANGRAU, 2010, 38(1) 86-102.

[7] A. Jamekhorshid, S. M. Sadrameli, and M. Farid, A review of microencapsulation methods of phase change materials (PCMs) as a thermal energy storage (TES) medium, Renewable and Sustainable Energy Reviews 31 (2014) 531-542].

[8] Fang Z and Bhandari B (2010) Encapsulation of polyphenols—a review. Trends Food Sci. Technol., 21: 510-523. <http://dx.doi.org/10.1016%2Fj.tifs.2010.08.003>

[9] Methavee Peanparkdee, Satoshi Iwamoto, Ryo Yamauchi, Microencapsulation: A Review Of Applications In The Food And Pharmaceutical Industries, Reviews in Agricultural Science, 4: 56-65, 2016. doi: 10.7831/ras.4.56.

[10] http://bioencapsulation.net/220 newsletter/BI_2013-03/Bioencap_innov_March_2013.pdf.

[11] Stephen M. HSU, and Fei ZHAO; Microencapsulation of Chemical Additives; US 2017/0073610 A1; Mar. 16, 2017.

[12] Farid, M., Al-Shannaq, R., Al-Muhtaseb, S. & Kurdi, J., Method for Low temperature microencapsulation of phase change materials, US 2018/0223146 A1, Aug. 9, 2018.

[13] Céline Dietlin, Stéphane Schweizer, Pu Xiao, Jing Zhang, Fabrice Morlet-Savary, Bernadette Graff, Jean-Pierre Fouassier and Jacques Lalevée; Photopolymerization upon LEDs: newphotoinitiating systems and strategies; Polymer Chemistry 6(21), June 2015.

[14] Niels Jorgen Madsen; David George Anderson; Bo Rud Nielsen; Novel Polymeric Photoinitiators and Photoinitiator Monomers; WO 2013/170858 A1.

What is claimed is:

1. An LED stirrer photoreactor for the photochemical microencapsulation or nanoencapsulation of a phase change active material with a curable material at an ambient or cold temperature for five minutes or less wherein the curable material comprises a mono-functional monomer and wherein the photoreactor comprises:
   (a) a transparent tube equipped with a helix stirrer that can be fit inside the tube; and
   (b) at least one LED lamp with adjustable light intensities.

2. The photoreactor of claim 1, further comprising a light reflector.

3. The photoreactor of claim 1, comprising more than one LED light.

4. The photoreactor of claim 3, wherein each LED light has a different light wavelength.

5. The photoreactor of claim 3, wherein each LED light has a similar light wavelength.

6. The photoreactor of claim 3, wherein each LED light has a different light intensity.

7. The photoreactor of claim 3, comprising two LED lamps wherein each has a wavelength of 365 nm and a radiation intensity of 0.6 W/cm$^2$.

8. The photoreactor of claim 3, comprising two LED lamps wherein each has a wavelength of 365 nm and a radiation intensity of 1.2 W/cm$^2$.

9. The photoreactor of claim 1, wherein the curable material further comprises a second mono-functional monomer or a di-, tri-, or poly-functional monomer.

10. The photoreactor of claim 1, wherein the transparent tube is rounded or square.

11. The photoreactor of claim 1, wherein the transparent tube is plastic or glass.

12. The photoreactor of claim 11, wherein the transparent tube is glass and is 3.5 cm in diameter.

13. The photoreactor of claim 1, for the microencapsulation or nanoencapsulation at an ambient or cold temperature for five minutes.

14. The photoreactor of claim 1, for the microencapsulation or nanoencapsulation at an ambient or cold temperature for less than five.

* * * * *